(12) United States Patent
Neitz et al.

(10) Patent No.: US 11,559,600 B2
(45) Date of Patent: Jan. 24, 2023

(54) DECONTAMINATION REACTOR FOR FLUID PURIFICATION

(71) Applicant: Ti-DOX Patent Inc., Calgary (CA)

(72) Inventors: Dean Richard Neitz, Calgary (CA); Reinhard Schuetz, Calgary (CA)

(73) Assignee: TI-DOX PATENT INC., Calgary (CA)

( * ) Notice: Subject to any disclaimer, the term of this patent is extended or adjusted under 35 U.S.C. 154(b) by 27 days.

(21) Appl. No.: 17/337,270

(22) Filed: Jun. 2, 2021

(65) Prior Publication Data

US 2022/0001070 A1     Jan. 6, 2022

(30) Foreign Application Priority Data

Jul. 3, 2020    (CA) ................................ CA 3085579

(51) Int. Cl.
     *A61L 9/20*           (2006.01)
     *B01D 53/00*        (2006.01)
     *B01D 53/88*        (2006.01)

(52) U.S. Cl.
CPC ............ *A61L 9/205* (2013.01); *B01D 53/007* (2013.01); *B01D 53/885* (2013.01); *A61L 2209/12* (2013.01); *B01D 2255/20707* (2013.01); *B01D 2255/802* (2013.01); *B01D 2259/804* (2013.01)

(58) Field of Classification Search
None
See application file for complete search history.

(56) References Cited

U.S. PATENT DOCUMENTS

| | | | |
|---|---|---|---|
| 4,798,702 | A | 1/1989 | Tucker |
| 4,956,754 | A | 9/1990 | Chen |
| 5,004,541 | A | 4/1991 | Noll et al. |
| 5,069,782 | A | 12/1991 | Moyer, Jr. et al. |
| 5,069,885 | A | 12/1991 | Ritchie |

(Continued)

FOREIGN PATENT DOCUMENTS

WO     WO-2006112605 A1 * 10/2006 ........... B01D 53/007

*Primary Examiner* — Jelitza M Perez
(74) *Attorney, Agent, or Firm* — WCF IP

(57) ABSTRACT

An apparatus for treating contaminated fluid has a UV lamp within an elongate housing, typically rectangular shaped. Deflector baffles within the housing create a meandering pathway perpendicular to the lamp for exposing the fluid to the UV light along the entire length of the pathway. Fins create multiple channels in the pathway to substantially increase internal surface area contact with the fluid. A photocatalytic coating on the baffles, fins and internal surfaces of the housing is maintained within a pre-set radial distance, preferably within about 75 mm, from the lamp for optimal creation of a photocatalytic reactant. The fluid flowing along the pathway, including channels, is also maintained in close proximity to the lamp and has adequate time for exposure to the ultraviolet light and photocatalytic reactant for treatment before exiting the housing. Baffles and fins are removably positioned within the housing for convenient maintenance, pathway length alteration or accommodating fluid volume flow adjustment, with little or no housing re-sizing. This apparatus is an affordable and compact environmental protection device capable of "air quality refinement", especially for building ventilation systems, by mitigating the spread of harmful pathogens and/or toxic chemicals.

20 Claims, 12 Drawing Sheets

(56) References Cited

U.S. PATENT DOCUMENTS

| | | |
|---|---|---|
| 5,501,801 A | 3/1996 | Zhang et al. |
| 6,932,947 B2 | 8/2005 | Leung |
| 10,633,266 B2 | 4/2020 | Schuetz |
| 2007/0084350 A1 | 4/2007 | Parker et al. |
| 2009/0041632 A1 | 2/2009 | Day et al. |
| 2009/0145855 A1 | 6/2009 | Day et al. |
| 2018/0265382 A1* | 9/2018 | Schuetz ............. B01D 53/8668 |

* cited by examiner

US 11,559,600 B2

DECONTAMINATION REACTOR FOR FLUID PURIFICATION

FIELD OF THE INVENTION

The present invention relates to a compact apparatus and method of treating contaminated fluids, and in particular treating such fluids via combined use of an energy source, such as a UV light, a photocatalytic reactant, enlarged contact surface area and a flow control arrangement, to economically and effectively target and destroy harmful contaminants therein.

BACKGROUND OF THE INVENTION

Since the turn of the last century, pollution from industrial operations and within air-tight buildings has increased dramatically and has been linked to detrimental health and environmental issues. Although somewhat controlled, both large and small scale emissions have a damaging cumulative impact on humans, animals and vegetation.

For example, in North America alone, yearly evaporative losses at retail fueling stations amount to about 1 billion litres of liquid gasoline (containing highly carcinogenic Benzene). With respect to air pollution (including 'sick building syndrome' issues), annual pre-mature human death toll is estimated at 8,000 in Canada, 200,000 in the USA and a staggering 7 million globally.

With statistics indicating that humans and domestic animals spending up to about 90% of their time in confined spaces (eg: buildings) as inspiration for the present invention, a decontamination device (known commercially as a "Ti-DOX Reactor") was created to simultaneously combat harmful organisms, noxious odours and toxic chemicals via "destruction at the source" (eg: predominantly at inlets and/or outlets of ventilation systems associated with environmentally sensitive and/or health related occupied confined spaces) to mitigate unnecessary transmission of contaminants and avoid detrimental health, safety and environmental issues. Furthermore, in anticipation of proposed requirements to limit energy consumption for heating, cooling and air conditioning of occupied spaces, reduced air change is expected to be implemented, which will increase air pollution within confined occupied spaces, and therefore should increase demand for the decontamination device of the present invention. It is also believed that the present decontamination device overcomes the limitations and disadvantages of prior art designs via simultaneous mitigation of germicidal and chemical hazards.

Prior art designs incorporate, individually, a photocatalytic coating, UV light and baffles within an enclosure to provide fluid purification. However, no known prior art combines all these components, nor incorporates multiple fins for substantially increasing photocatalytic coated surface areas, into the same device for effective fluid decontamination. The present invention manages to create an unrestricted fluid (gas and/or liquid) pathway, as well as provide continuous direct line-of-sight UV light exposure for fluid and photocatalytic coated surfaces, with the intention of enhanced purification of contaminated fluid along the pathway.

One example of a pathway created with a baffle or tube arrangement is shown in U.S. Pat. No. 5,004,541 (Noll et al.) However, this patent lacks features critical to effective treatment of fluids, and the types of pathways shown are not optimal for, or are incapable of, exposing the fluid to a desired level of UV light for destruction of both harmful biological organisms and toxic chemicals.

Other prior art designs have incorporated UVC light with desirable photoreactive coatings and flow control systems. However, the pathway designs provide sub-optimal exposure to a desired level of UV light, and exposure to surface coatings is not optimized for effective decontamination. Some examples are shown in U.S. Pat. No. 5,069,885 (Ritchie), U.S. patent application Ser. No. 11/951,520 (Day et al.) and U.S. Pat. No. 4,956,754 (Chen).

What is therefore desired is a novel improved apparatus and method for treating contaminated fluids to overcome the limitations of existing designs. Preferably, it should consist of a single device to combat both hazardous biological organisms and toxic aromatic chemical compounds. It should provide a cost effective compact housing complete with inlet/outlet connections, UV lamp, internal photocatalytic coating and a specially designed internal baffle and fin system that is removably positioned within the apparatus for ease of maintenance and alteration, as needed. The combination of these features should not only allow for continuous and extended fluid exposure to UV light within the housing, but should also confine the maximum distance from the lamp to all internal coated surfaces in order to achieve a highly effective photocatalytic reaction. In addition, the present invention should also allow for sequential interconnecting of numerous reactors, either in parallel, in series, side by side or via stacking, and whether consisting of single or multiple UV lights, to achieve increased volume treatment of contaminated fluids entrained either with harmful pathogens, toxic chemicals or noxious aromatic elements.

SUMMARY OF THE PRESENT INVENTION

Therefore, according to the present invention, there is provided in one aspect an apparatus for treatment of a contaminated fluid comprising:

an elongate housing having a length and an inlet and an outlet in an outer wall thereof, wherein said inlet receives said contaminated fluid and creates at least one fluid stream thereof;

at least one elongate energy source for emitting energy extending within said housing along the length thereof;

at least one baffle arranged in a spaced relationship along the length of said elongate housing and oriented generally perpendicular to said elongate energy source, and extending radially between said elongate energy source and said outer wall of said elongate housing, said at least one baffle defining an opening at least at one end thereof wherein said opening is located to create a meandering pathway generally perpendicular to said elongate energy source for said fluid stream from said inlet to said outlet to provide uninterrupted exposure to said energy from said elongate energy source along the length of said meandering pathway;

at least one fin located along a portion of said meandering pathway and spaced from said at least one baffle for subdividing said portion of said meandering pathway into a plurality of flow channels; and, a photocatalytic coating on said at least one baffle, said at least one fin and inner surfaces of said outer wall of said elongate housing, wherein said inner surface of said outer wall of said elongate housing is within a pre-set radial distance of said elongate energy source for exposure to said energy to activate a photocatalytic reactant, so that said contaminated fluid flowing through said meandering pathway, including said flow channels, is continuously maintained within said pre-set radial distance to said elongate energy source and is provided adequate time flowing along said meandering pathway for combined exposure to said energy and said photocatalytic reactant to treat said contaminated fluid before exiting said elongate housing through said outlet.

BRIEF DESCRIPTION OF THE DRAWING FIGURES

Embodiments of the invention will now be described, by way of example only, with reference to the accompanying drawings, wherein.

Figure 1:
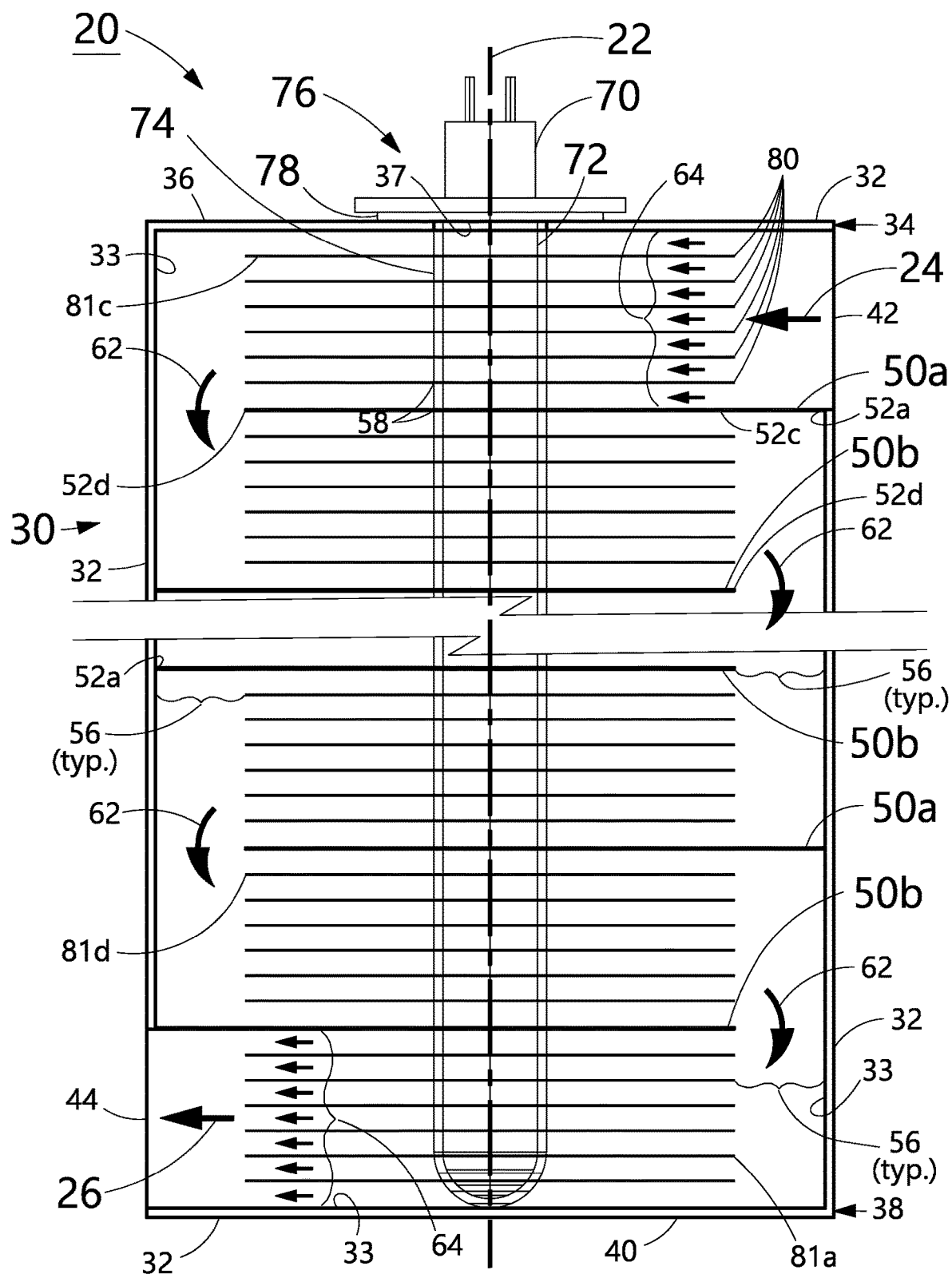
FIG. 1 shows a transparent plan view of a UV light reactor according to a preferred embodiment of the present invention.

LIST OF REFERENCE NUMBERS IN DRAWINGS 20 reactor
22 longitudinal axis of 20
24 incoming contaminated fluid stream
26 discharged treated fluid stream
30 housing of 20
32 rectangular outer wall of 30
33 inside surface(s) of 32
34 first/top end of 30
36 first lid assembly at 34
37 hole in 36
38 second/bottom end of 30
40 second lid assembly at 38
42 inlet port of 30
43 extended inlet connection (variant of 42)
44 outlet port of 30
45 extended outlet connection (variant of 44)
50a/b (deflector) baffles
52a/b/c/d edges of 50a/b
55 openings for lamp in 50 and 80
56 end openings between 52 and 33
58 edge of 55
59 optional cut-out opening in 50a/b
62 meandering pathway
64 (flow) channels of 62
70 lamp arrangement
72 lamp of 70
74 sleeve of 72
76 mounting assembly of 72
78 gasket of 76
80 fins
81a/b/c/d edges of 80
82a/b optional cut-out openings in 80
90/91 ventilation duct(s)
100 spacer tabs
101 baffle/fin plate
102 spacer guide
103 longer/shorter slits in 102

DESCRIPTION OF PREFERRED EMBODIMENTS

The figures show a reactor (generally designated by reference numeral 20) whose energy source is a lamp arrangement 70 having an elongated lamp 72 for emitting ultraviolet light or radiation (sometimes referred to herein as a "UV light" or "UV lamp"). In the preferred embodiment UVC light is desired, and thus a "UVC lamp" 72 is provided along the reactor's central longitudinal axis 22. The reactor 20 consists of an rectangular elongated hollow tubular housing 30 for containing the lamp arrangement 70, deflector baffles 50a/b and fins 80, hereafter generally referred to as "baffles" and "fins", respectively. The purpose of the reactor is for treating an incoming contaminated fluid stream 24 before being discharged as a treated fluid stream 26. Contaminated or treated fluid streams may hereafter sometimes be referred to simply as "fluid".

In the preferred embodiment of FIG. 1, the housing 30 is defined by an outer wall 32 of rectangular cross-section which is fluidly sealed at its opposed ends, namely at a first (or top) end 34 by a first lid assembly 36, and at a second (or bottom) end 38 by a second lid assembly 40. Depending on the type of contaminated fluid being treated, preferred materials for the housing (aka "container") include galvanized sheet metal, aluminum and/or stainless steel. It is anticipated that in use the reactor 20 will typically be oriented horizontally, namely rotated 90 degrees to the upright position shown in FIG. 1, but advantageously any orientation is suitable for operation of the device. Nonetheless, terms such as "top" or "bottom", "left" or "right", and the like will be used for ease of identifying certain features of the reactor in the orientation shown in the figures. Employment of these terms is not intended to limit the reactor's orientation in use. Further, when describing the invention, all terms not defined herein have their common art-recognized meaning.

Figure 4:
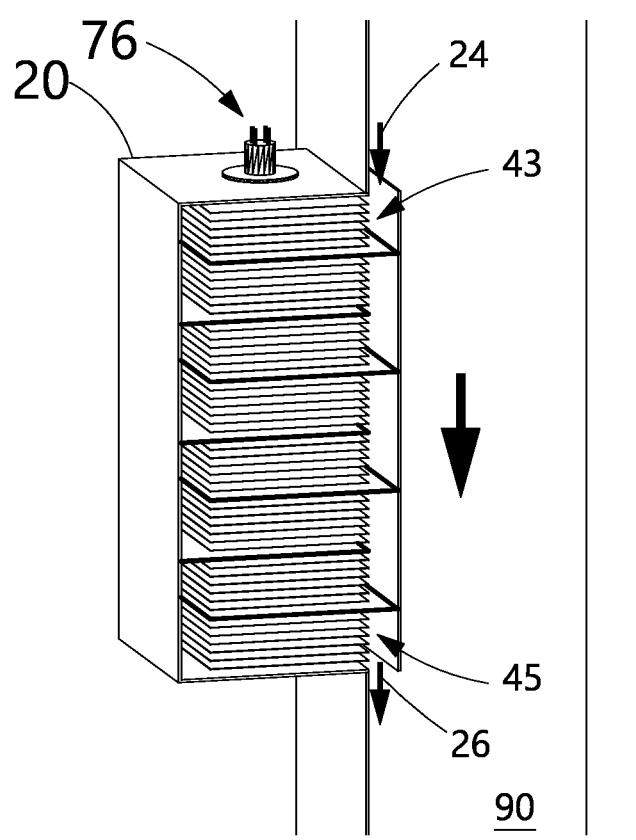
FIG. 4 shows a typical reactor installation, namely the reactor of FIG. 2B mounted outside a ventilation duct with the reactor's inlet and outlet openings located inside the duct to intercept at least some of the fluid flow therein.
Figure 5:
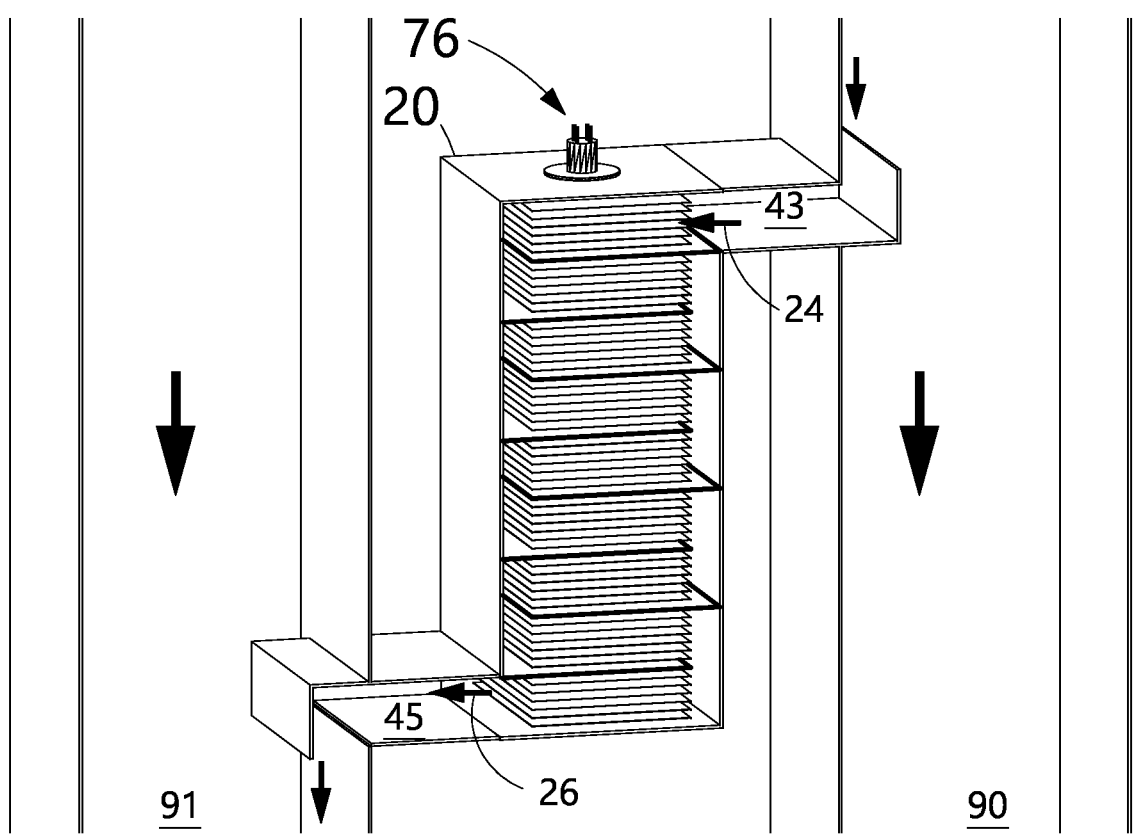
FIG. 5 shows a typical reactor installation similar to that shown in FIG. 4, but cross-connecting two ventilation ducts.
Figure 6A:
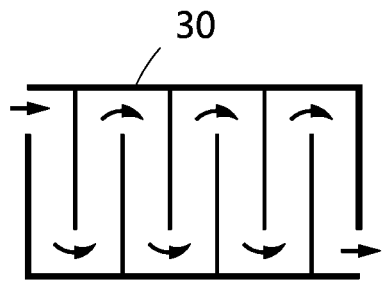
FIGS. 6A to 6E illustrate, in plan view similar to FIG. 1, various versions of inlet/outlet locations and housing sidewall configurations.
Figure 6B:
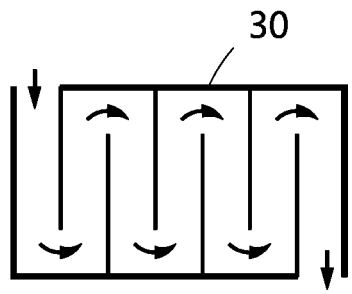
Figure 6C:
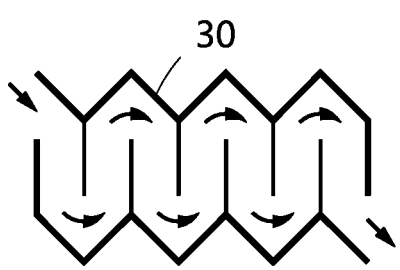
Figure 6D:
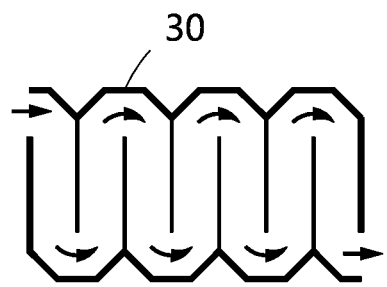
Figure 6E:
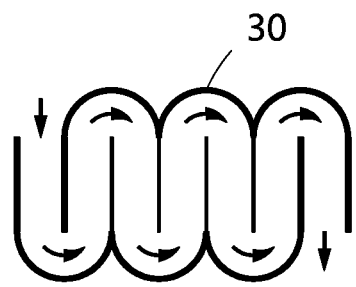
Figure 7A:
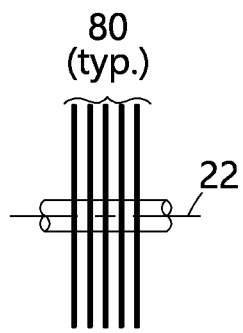
FIGS. 7A to 7D illustrate several design and installation configurations of the fins shown in FIG. 1.
Figure 7B:
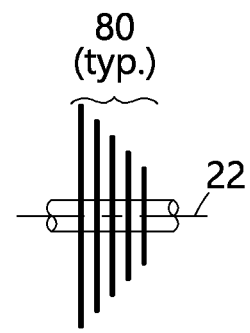
Figure 7C:
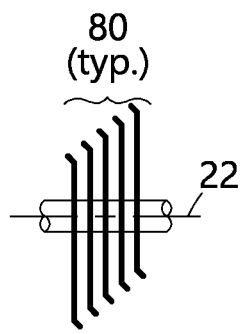
Figure 7D:
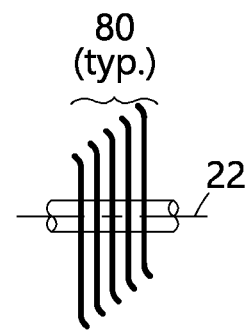
Figure 8A:
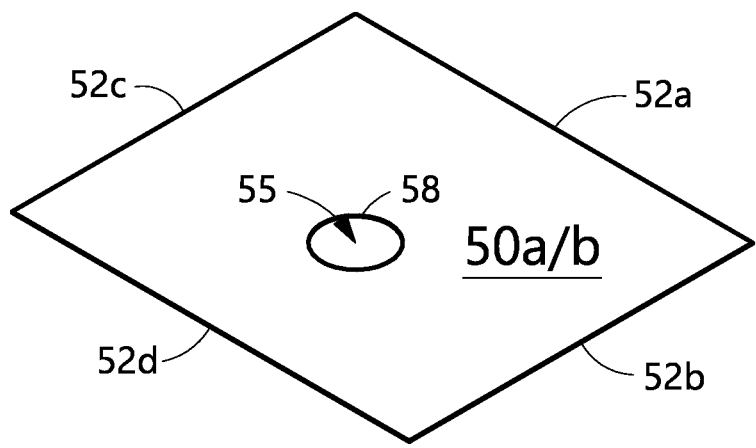
FIG. 8A is a perspective view of a baffle installed lengthwise generally non-symmetrically to a UV lamp hole (allowing for fluid flow passage at the end nearer to the UV lamp hole)
Figure 8B:
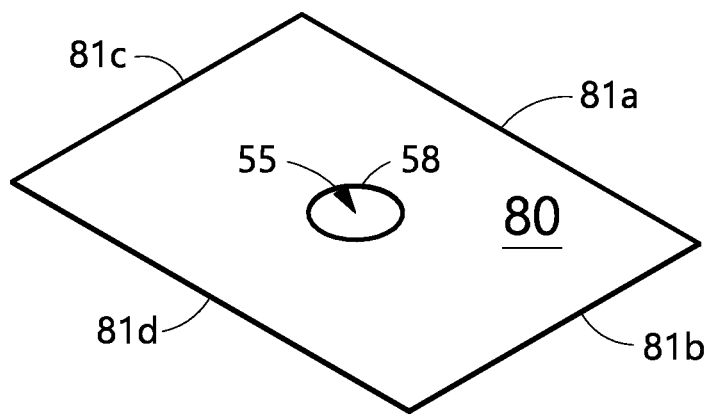
FIG. 8B is a variant of FIG. 8A showing a fin installed generally symmetrically around the UV lamp hole (allowing for equally spaced fluid flow passage on two opposing sides from the UV lamp hole)
Figure 9A:
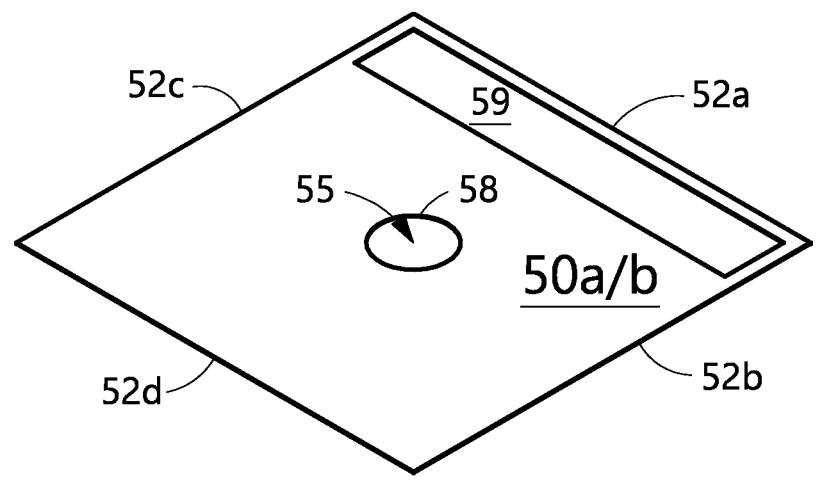
FIG. 9A is a perspective view of a baffle installed symmetrically around the UV lamp hole, allowing for fluid flow passage at one end to the UV lamp hole via an elongate cut-out opening.
Figure 9B:
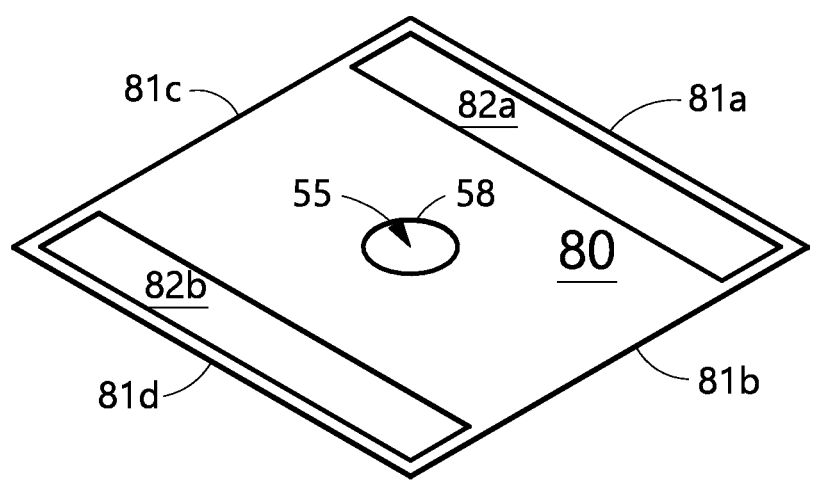
FIG. 9B is a variant of FIG. 9A showing a fin installed symmetrically around the UV lamp hole, allowing for equally spaced fluid flow passage on two opposing sides from the UV lamp hole via two elongate cut-out openings.
Figure 10A:
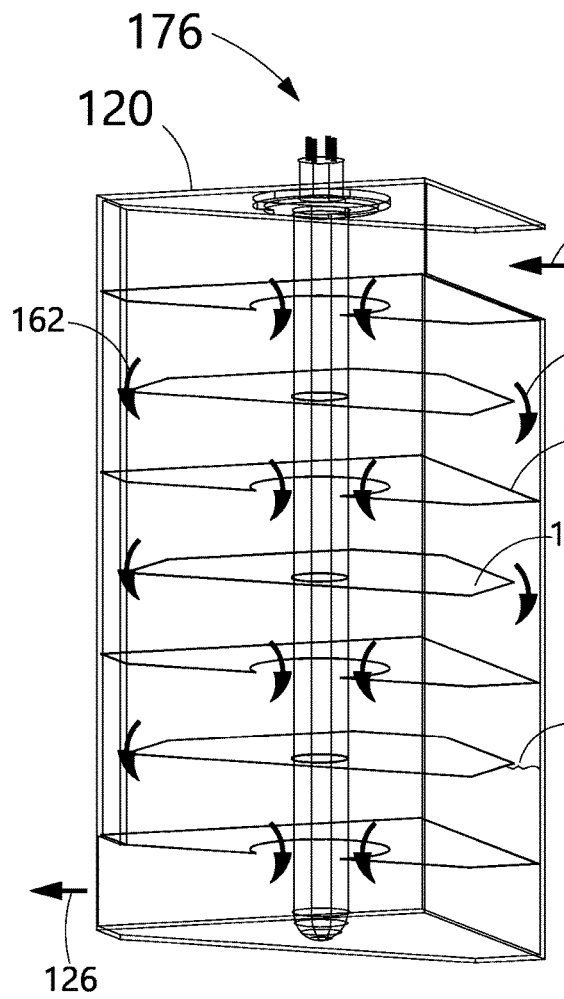
FIG. 10A is a variant of the embodiment in FIG. 2A showing a modified baffle design allowing fluid flow to alternately circumvent the outside and inside edges of alternate groupings of baffles.
Figure 10B:
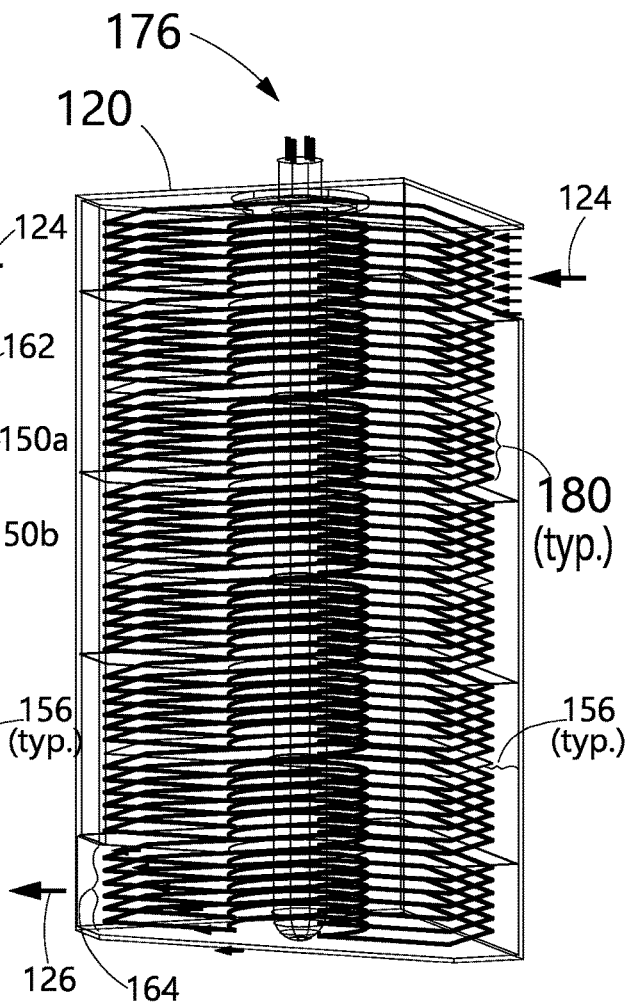
FIG. 10B shows the reactor of FIG. 10A with fins installed.
Figure 11A:
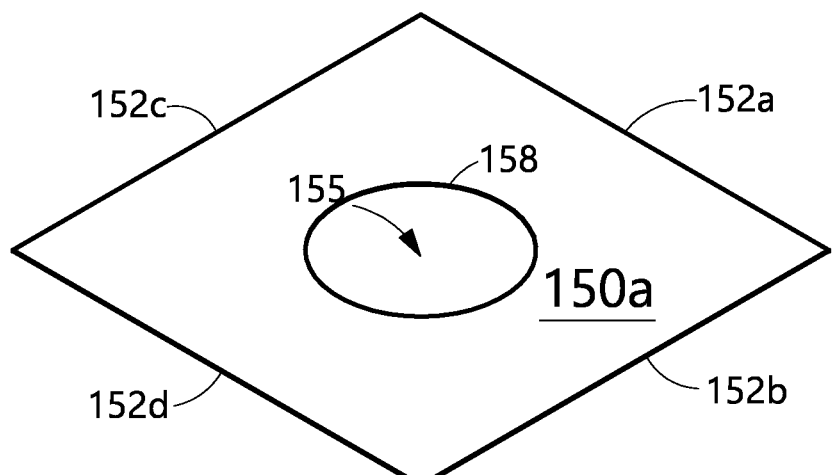
FIG. 11A is an isolated view of a first baffle type in the reactor of FIG. 10A having a larger central lamp opening with an expanded inside edge for allowing fluid flow therethrough.
Figure 11B:
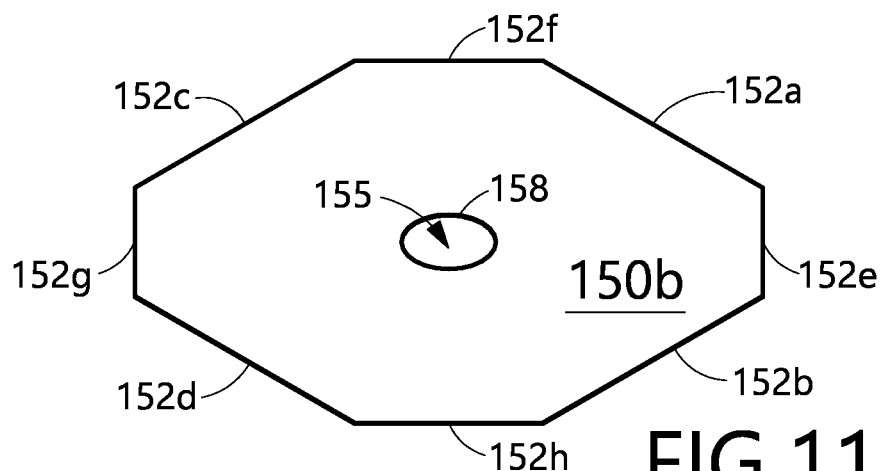
FIG. 11B is an isolated view of a second baffle type in the reactor of FIG. 10A having cut-off corners to create outside edges for allowing fluid flow therethrough.
Figure 11C:
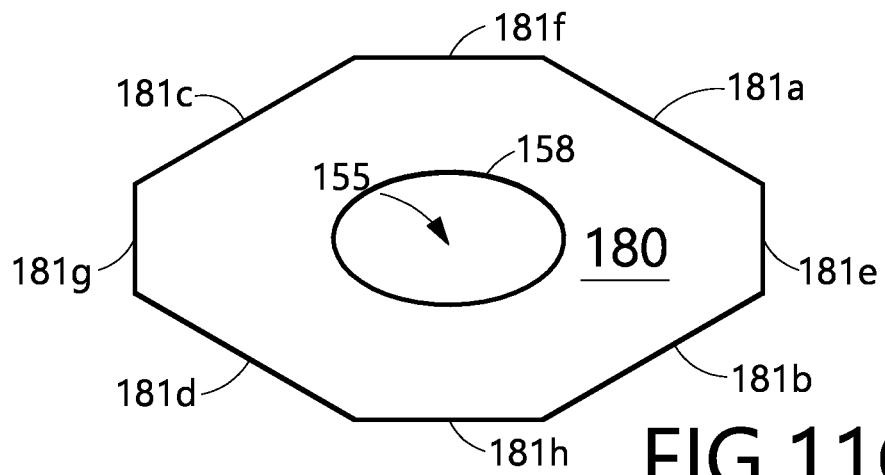
FIG. 11C is an isolated view of a fin in the reactor embodiment of FIG. 10B having both a larger central lamp opening with an expanded inside edge and cut-off corners to create outside edges, allowing fluid flow through both; and, FIGS. 12A and 12B show two spacer configurations, namely spacer tabs and spacer guides respectively, for both baffles and fins.

In the FIG. 1 embodiment of the reactor, the housing's outer wall 32 has an inlet port 42, or extended inlet connection 43 (illustrated in FIGS. 4 & 5), both hereafter sometimes referred to as "inlet", in addition to an outlet port 44, or extended outlet connection 45 (also in FIGS. 4 & 5), hereafter sometimes referred to as "outlet". The reactor housing is configured to be operatively coupled in a fluid tight manner to a supply of contaminated fluid 24 (illustrated in FIG. 4 as ventilation duct 90) which after being treated in the reactor is discharged as treated fluid 26 back into the same duct 90, or into a different duct 91 (as per FIG. 5), or elsewhere. The supply delivers the fluid to the inlet 42/43 either by mechanical means (e.g. pump, fan, suction, etc) or non-mechanical means (e.g. gravity, evaporation, etc). Depending on environmental conditions, and considering that the reactor is not designed to capture particulate matter in the fluid supply, a particulate filter (not shown) may optionally be installed to intercept the fluid supply upstream of the reactor inlet.

The inlet 42/43 and outlet 44/45 are both shown as rectangular, as that is most typically the shape of the ducting or piping to which they will be coupled either via clamping, flanging or any other form most suitable to the operational environment. In the FIG. 1 configuration, as well as the other illustrated versions, there is a single inlet 42 and outlet 44 shown. The incoming fluid stream 24, after entering inlet 42, is directed into a meandering pathway created between the baffles 50a and 50b situated perpendicular to the longitudinal axis 22 of the UV lamp, in a single stream towards outlet 44 at the opposite end. The cross sectional area between adjacent baffles 50a/b, baffle end openings 56, and outlet 44 is configured slightly larger compared to the inlet 42 cross sectional area in order to accommodate the flow capacity of fluids 24 & 26 without creating flow restriction and/or back pressure. However, it will be appreciated that the incoming fluid 24 might also be proportioned upstream of the reactor to arrive in separate streams, and thus the inlet 42 may be configured to be multiple openings at appropriate positions on the housing's outer wall 32. Likewise, the outlet 44 may take the form of two or more ports if need be.

The reactor's lamp arrangement 70 extends substantially along the length of the housing 30 between the first and second ends 34 & 38. The UV lamp 72 is housed within a clear and fluid tight tubular sleeve 74, such as those made of high quality quartz, to avoid contact with fluid inside the reactor when mounted therein. Instead of, or in addition to the sleeve, the UV lamp 72 may be covered in a tight fitting clear Teflon (or equivalent material) to prevent fluid contact and avoid personal injury in case of lamp breakage when being handled by an operator. The lamp and sleeve are supported from the lid 36 at the top end 34 of the container, and may optionally have some support at the bottom end 38, as well as at locations between the top and bottom ends 34, 38. In the FIG. 1 embodiment the top end of the lamp and sleeve are fixed to a mounting assembly 76 which, after the lamp and sleeve are inserted into the container through a lid hole 37 in the lid assembly 36, has a flange for forming a fluid seal about the lid hole 37, with the aid of a gasket 78 or the like if needed. The mounting assembly 76 is preferably removably secured to the lid 36 via appropriate means such as fastening the flange to the lid or by using a clamped connection to cover the lid hole 37, so that an operator may readily remove the lamp from the container for cleaning the sleeve, replacing the UV lamp assembly 70, or other maintenance. It will be appreciated that the lamp's mounting assembly 76 may be permanently connected to the lid 36, thus requiring removal of the lid for access to the lamp, but such arrangement is less convenient and thus not preferred. The mounting assembly 76 is operatively coupled to a source of power (not shown).

The plurality of baffles 50a/b and fins 80, each in the form of generally planar thin plates, are perpendicularly spaced along the UV lamp assembly 70 within the housing 30 (as best seen in FIG. 1). Each baffle 50a/b extending in an alternating pattern between inlet 42 and outlet 44 and from opposite sides of the inside surface 33 of the housing's outer wall 32, and each fin 80 is optimally spaced between the baffles with fin openings at each end corresponding to each baffle 50a/b opening. In the preferred embodiment, all baffles 50a/b are generally the same length, and all fins 80 are generally the same length. The baffles and fins have holes, or openings, 55 which are longitudinally aligned within the housing to accept the lamp arrangement 70 therethrough. A snug fit is provided, preferable but not necessary, between edge 58 of the UV lamp opening 55 in baffles 50a/b and in fins 80 with the outer surface of the lamp assembly 70, as well as between the baffle edges 52a/b/c and fin edges 81b/c to the applicable inner surface 33 of the housing wall 32, so as to minimize or eliminate fluid seepage through those interfaces (see also FIGS. 8A to 9B).

While baffle edge 52a of each baffle 50a is meant to abut to a housing inner side wall surface 33, baffle edge 52d is spaced away from the opposite inner side wall surface 33, thereby forming an opening 56 between baffle edge 52d and adjacent side wall inner surface 33. Conversely, baffle edge 52a of each baffle 50b is meant to abut on the housing's opposite side wall's inner surface 33, thus spacing baffle edge 52d away from the opposite inner surface 33, thereby forming an opening 56 between baffle edge 52d and adjacent side wall inner surface 33. Thus, baffles 50a/b form an alternating series of baffle openings 56 along the axial length of the housing 20 to form a continuous meandering pathway 62 between the inlet 42 and outlet 44.

Fin edges 81a and 81d of each fin 80 (shown in FIG. 8B) are spaced away from each adjacent side wall inner surface 33 so as for each to achieve an opening cross-sectional area equivalent to openings 56 (associated with baffles 50a/b) of the meandering pathway. Optionally, all four edges of each baffle 50a/b and fin 80 could be sized to respectively abut to all four side wall inner surfaces 33 and, in order to maintain a continuous meandering pathway 62, be designed with cut-out baffle openings 59 (shown in FIG. 9A) to match the flow-through area of the openings 56 of the meandering pathway of the preferred embodiment; and likewise cut-out fin openings 82a/b (shown in FIG. 9B) also each matching the openings 56 of the meandering pathway in cross-sectional area at each fin end. Therefore, instead of only baffle edges 52b/c and fin edges 81b/c abutting the housing's inside surface 33, additionally baffle edges 52a/b and fin edges 81a/b may now also abut to the inside surfaces 33. Hence, as best seen in FIG. 1, the sequentially spaced arrangement of baffles 50a/b, coupled with the alternating arrangement of baffle openings 56 or 59, and fin openings 56 or 82a/b, creates the distinct meandering pathway 62 oriented generally perpendicular to the longitudinal axis 22 and the UV lamp 72, for directing the fluid 24 from the inlet 42 to the outlet 44. The pathway 62 terminates at the outlet 44 to allow the fluid 24, now having been converted to treated fluid 26, to discharge from the reactor.

Figure 12A:
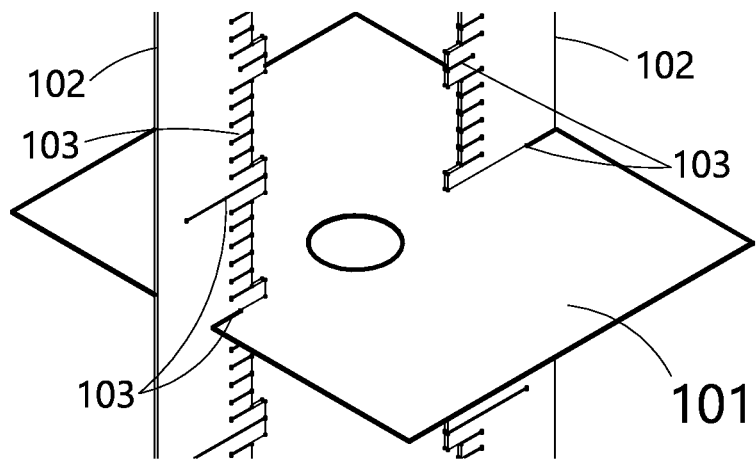
Figure 12B:
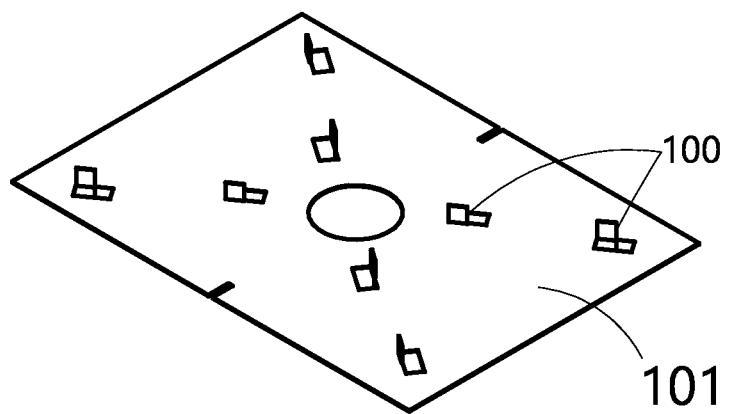

To avoid creating potential fluid flow channel restrictions due to deflection of the generally planer thin plates forming the baffles or fins, each baffle and fin may include integrated or separate perpendicular extensions as a means to achieve consistant spacing between adjacent fins 80, fin 80 adjacent to baffles 50a/b, and fin 80 adjacent to end lids 36/40. FIG. 12B illustrates a series of spacer tabs 100 either integral to the baffle/fin plate 101, such as by punching out the metal plate upwardly, downwardly or both, or secured to the upper and/or lower surfaces of the plate such as with an adhesive, for abutting an adjacent plate thereabove and/or therebelow. The tabs 100 are preferably aligned radially outwardly from the central lamp opening to avoid obstructing UV light direct line-of-sight to the periphery of the reactor. FIG. 12A illustrates an alternate spacer configuration where vertically oriented spacer guides 102 employ linearly aligned slits 103 for supporting each baffle/fin plate 101. The slit lengths may vary (as illustrated) to position different baffle/fin plates. The spacer guides 102 should likewise be oriented radially outwardly to avoid obstructing UV light to the reactor's outer periphery.

Figure 3A:
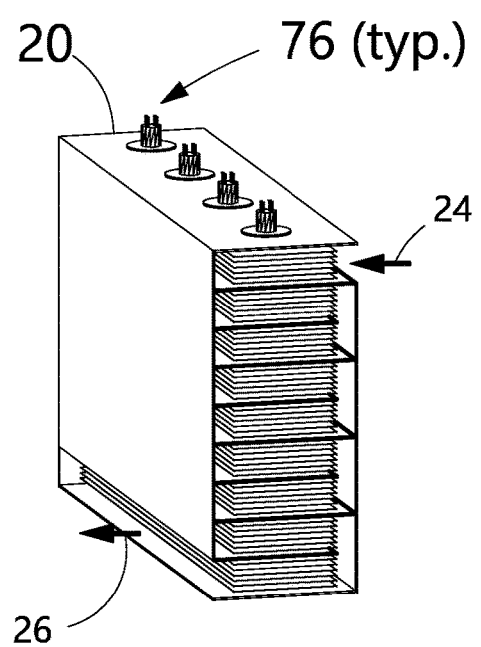
FIG. 3A is a perspective view with one side open similar to FIG. 2B illustrating another embodiment of the reactor with a plurality of UV light assembly installations and adjusted baffle and fin sizes, namely a version having a row of four UV lights spaced along longer baffles and fins than in FIG. 2B.
Figure 3B:
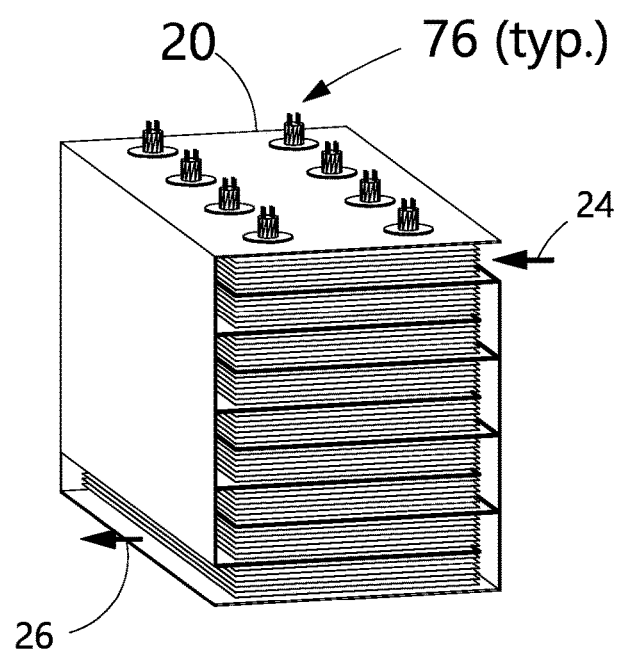
FIG. 3B is a view similar to FIG. 3A but illustrating yet another embodiment of the reactor having two parallel rows of four UV lights each spaced along wider baffles and fins than those of FIG. 3A.

It will be appreciated that for a given size of housing 30 and a given fluid flow volume, the spacing (as in FIG. 1) between each pair of baffles 50a/b could in part determine the fluid velocity along the pathway 62 through the reactor housing, namely a tighter spacing with more baffles will increase fluid velocity compared to a more expansive spacing with fewer baffles. In addition, fluid decontamination can also be influenced by the size of the housing, namely by augmenting or contracting the length, width or height of the fluid pathway 62 between the inlet and outlet. Based on specific requirements, the housing size and number of UV lamps (as shown in alternate embodiments in FIGS. 3A and 3B, and discussed later) should be determined prior to manufacture of the reactor housing and is effectively fixed thereafter. However, the number and spacing of removably positioned baffles 50a/b and fins 80, can be altered at any time by a user to suite a particular operation change, which is a highly beneficial advantage of the present invention.

Figure 2A:
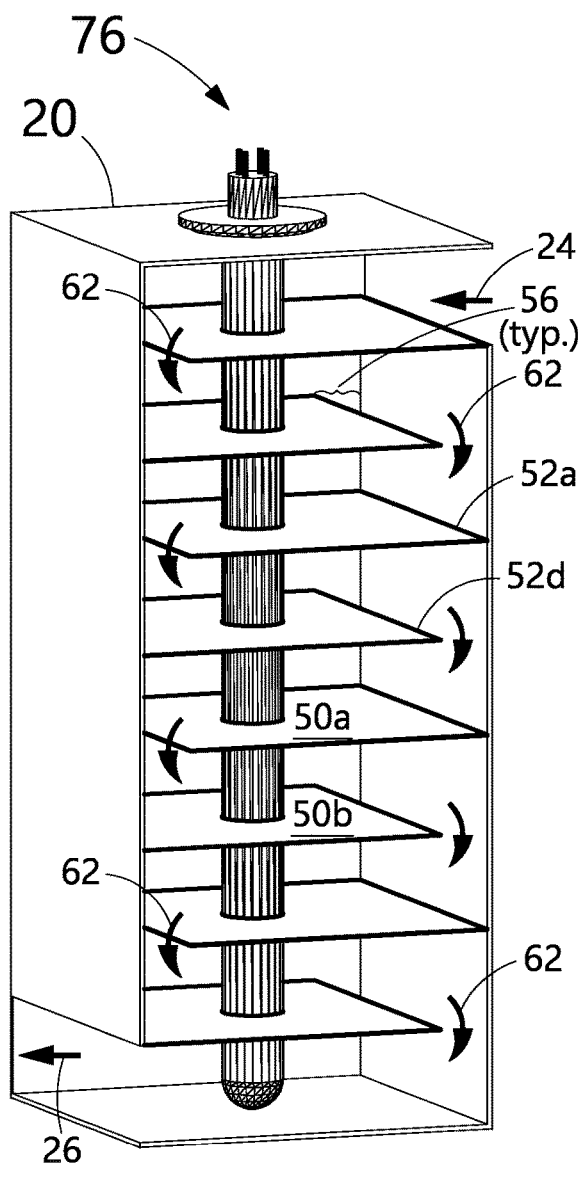
FIG. 2A shows a perspective sectional view of the reactor of FIG. 1 in an upright "operational" position, with one exterior side removed for viewing the interior configuration of deflector baffles, UV light and inlet/outlet openings, but omitting fins.
Figure 2B:
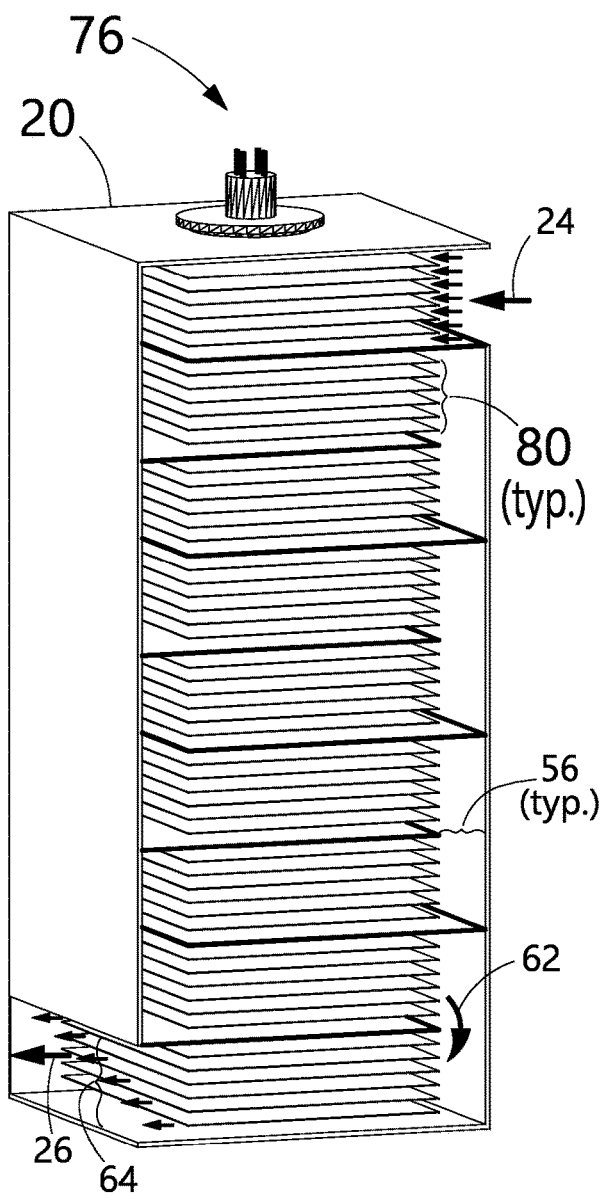
FIG. 2B shows the reactor of FIG. 2A with fins included.

An important feature of this reactor design is the ability to provide continuous full exposure of fluid passing through the reactor to the light emitted from the energy source, and to a Titanium Dioxide (TiO$_2$) coating (discussed below). This is advantageously achieved in large part by subdividing large segments of (i.e. most of) the meandering pathway 62 into a plurality of parallel fluid flow channels 64 (as best seen in FIGS. 1 and 2B). The channels 64 created between the spaced baffles 50a/b and fins 80 provide maximum opportunity of interaction of the radially emitted UV light, coated surfaces and meandering fluid being treated without creating shadowed areas, blind corners and such, and without obstructing fluid flow through the reactor.

The reactor 20 of the present invention also incorporates a photocatalytic material to enhance the treatment of the incoming contaminated fluid 24. A Titanium Dioxide (TiO$_2$) Anatase coating has been found to be highly effective, although equivalent photocatalysts may be suitable as well. The reactor's unique design, aside ease of fabrication, assembly, installation and maintenance, provides three particular novel and beneficial advantages for the use of this photocatalyst.

First, the reactor's specific baffle configuration optimizes internal surface area available for photocatalytic coating application. In the preferred embodiment the photocatalytic coating is provided on all surfaces of the baffles 50a/b, the numerous fins 80, the inside surfaces 33 of the housing and the inner surfaces of the extended inlet and outlet connections 43, 45.

Second, the installation of one or more fins 80, preferably in the form of thin, flat, metallic plates. Numerous fins are optimally spaced along the length of the UV lamp assembly 70, namely the fins should be spaced substantially equally and in parallel to avoid creating fluid flow restrictions between adjacent baffles 50a/b, or between baffles 50a and/or 50b adjacent to their respective housing end lid assemblies 36 and 40. Such installation of fins provides critical added photocatalytic coating area for the generation of copious amounts of Hydroxyl Radical reactants, considered the most powerful cleaning agents found in the earth's Troposphere for destroying harmful biological organisms and oxidizing (aka "cracking" or 'breaking") molecular bonds of toxic chemical compounds in contaminated fluid.

Third, by limiting the distance of all photocatalytic coated baffles 50a/b, fins 80 and housing internal surfaces 33 to about 75 mm from the UV light, this invention's configuration ensures continuous, unimpeded and effective coating-to-UV light interaction along the entire length of the fluid pathway 62, throughout the reactor. It has been found that a distance of no more than about 75 mm maintains continuous "optimal", namely substantially complete, activation of photocatalytic reactant by the UV light for effective decontamination of the fluid. It appears that beyond a distance of about 75 mm, propagation of UV light intensity decreases exponentially with increasing distance from the UV light source in accordance with the 'inverse square law'—that is, only about a quarter intensity of the UVC remains with each doubling of the distance. Therefore, photocatalytic coating effectiveness is substantially decreased in creating the desired amount, or concentration, of reactant, such as Hydroxyl Radicals.

Aside from achieving improved photocatalytic reactant generation of Hydroxyl Radicals, limiting the distance between the housing's inside surfaces 33 and the UV light also adds to improved inactivation of harmful pathogens via direct UV light contact alone. Biological organism (bacterium, viruses, spores, etc.) sterilization is interrelated between UV light intensity and exposure time. That is, greater UV light intensity at contact results in shorter required time duration for germicidal DNA/RNA inactivation to avoid further reproduction. At a 1 m (meter=about 3.3 feet) distance, typical UVC lamps emit a light intensity averaging roughly 300 $\mu W \cdot s/cm^2$. The average required intensity for effective 99% germicidal destruction at 1 m distance amounts to approx. 23,500 µW·s/cm². Therefore, it becomes apparent that continuous 'close proximity' contact with UV light is a critical reactor design feature, not only for direct exposure of contaminated fluid to UV light, but also for the heat produced by the lamp to assist in the destruction of germs, and the generation of copious amounts of Hydroxyl Radicals to facilitate the destruction of toxic chemicals.

The amount of surface area coated with photocatalytic reactant within a given size of container can be advantageously altered by adjusting the number of removably positioned baffles 50a/b and/or fins 80. To illustrate, adding more baffles to the housing not only increases the length of the resultant fluid pathway 62 but increases surface area available for coating with photocatalytic material. Similarly, although not increasing pathway 62, the addition of more fins also increases the number of flow channels in the pathway and expands the available surface area for photocatalytic coating application. Hence, the increased number of baffles and/or fins substantially increases the amount of produced reactant, and thus increases the desirable interaction between the fluid and reactant along the also lengthened pathway. It will be further appreciated that the amount of coated surface area of the generally rectangular housing shown in FIG. 1 may be altered, as shown in FIGS. 6A to 6E, to suit specific operating parameters, and likewise the shape and configuration of the fins may be suitably varied as shown in FIGS. 7A to 7D.

Assembly of the housing's interior features is a relatively simple matter of: (a) applying a photocatalytic coating on all of the housing's exposed inside wall surfaces 33; (b) positioning and spacing a plurality of baffles 50a/b in such a manner as to avoid creating a fluid flow restriction; (c) positioning and spacing the plurality of fins 80 between the baffles without creating a fluid flow restriction, and (d) inserting and centrally positioning an energy source (typically UVC light) through the lid opening 37, along the central axis 22 of the housing such that the lamp sleeve 74 abuts all the baffle and fin openings 55 on the inside edges 58. Upon attaching a cover over the open sections of housing 30 and securing the lamp's mounting assembly 76 to the lid 36, the reactor 20 is ready for installation to inlet/outlet sources, and to a power source for controlling operation of the UV lamp.

The baffles and fins of the present invention may be provided with a series of grooves or surface corrugations, such as a sinusoidal or crimped pattern, radially outward from the central axis 22 across each baffle, thereby creating a 'washboard' effect and providing increased $TiO_2$ coated surface area exposure to UVC light. Other modified irregular baffle surface configurations could also be provided, such as dimples, cross-hatched corrugations, or longitudinal ripples, but they may not be preferred as they could reduce direct line-of-sight UV light contact with the $TiO_2$ coating due to shadow effect on the far side of the dimples, ripples or cross-hatched corrugations.

In operation, the incoming contaminated fluid 24 through the housing's inlet 42 will begin an extended journey by following the meandering pathway 62 (and through the flow channels) created by the arrangement of deflector baffles 50a/b and fins 80 (best seen in FIG. 1). By the time the fluid stream 24 has traversed from the inlet 42 to the outlet 44, it will have travelled, predominantly perpendicular to the central axis 22, the equivalent of about nine (9) lengths of the housing. In addition, the fluid has an equivalent of about a nineteen (19) fold greater exposure to photocatalytic coated surface area, as compared to a single straight flow-through reactor design. Throughout this travel along the meandering pathway 62, based on the preferred embodiment of this invention, the fluid stream remains within a constant distance, preferably 75 mm or less, from the lamp assembly 70 and all photocatalytic coated surfaces, and is consistently bathed in Hydroxyl Radicals generated via the interaction of UV light and $TiO_2$ coating. Being perpetually subjected to UV light and Hydroxyl Radicals within the reactor, the fluid arrives at the outlet 44 and is discharged as treated fluid 26.

The reactor's lamp sleeve 74 may require periodic cleaning to avoid undue obstruction of UV light from the lamp into the housing 30. This is easily achieved by merely suspending incoming fluid, but not necessarily air flow, disconnecting the lamp assembly from the lid 36 and removing it from the housing via the lid hole 37. The sleeve may then be cleaned and the UV lamp inspected (and replaced if need be), and the lamp assembly can then be returned into the housing as previously described, with minimal disruption to the operation of the reactor.

The many advantages and further aspects and features of the present invention may now be better understood.

For a given size of reactor, the pathway may be advantageously lengthened, or shortened if need be, by altering the number of baffles (and adjusting the number of fins) between the housing's inlet and outlet, without altering the reactor's length or other external dimensions. An important added benefit of increasing the pathway, by adding baffles and especially fins to subdivide almost all the pathway into numerous flow channels, is the substantial increase in surface area coated with photocatalytic material, thereby increasing the production of desirable photocatalytic reactant to treat the fluid stream, along the now longer pathway. This "multiplied benefit" is not achieved in prior art devices for this purpose, with such ease, and without having to re-size or re-build any prior art equipment.

The configuration of the reactor of the present invention advantageously positions and maintains a distance, typically about 75 mm, of the UVC lamp to all $TiO_2$ coated surface areas inside the housing for sufficient, or "full", exposure of the coating to the UV light for substantially complete activation of photocatalytic reactant. It has been observed that, within this preferred distance, the photocatalytic reaction of UVC light with $TiO_2$ is most effective in creating Hydroxyl Radicals that are integral to sterilizing bacterial organisms and 'cracking' (i.e. oxidizing) molecular bonds of toxic chemicals. Hydroxyl Radicals are capable of generating almost one and a half (1.5) times the oxidation power compared to Ozone ions. In addition, Hydroxyl Radicals are short lived (less than one second), thus all reactions are contained within the reactor 20, rather than lingering in the atmosphere for hours or days like hazardous Ozone. Also, being a photocatalyst, $TiO_2$ undergoes virtually no depletion during the photocatalytic process.

The design of the present reactor allows for numerous optional inlet/outlet location placements and reconfiguration of baffle and fin designs in virtually any combination to efficiently achieve increased contaminated fluid volume treatment if required, without reducing the effectiveness of fluid decontamination, nor requiring major configuration changes, nor the inconvenience of joining multiple reactors 20. One such variant is illustrated in FIGS. 10A to 11C which show a reconfigured interior resulting in an altered meandering pathway 162 using modified baffles 150a/150b and fins 180. The reference numerals used for this variant are similar to those used to identify the components of the preferred embodiment of the reactor 20 (in FIGS. 1 to 3 and 8A/B), with the addition of a prefix '1'. Incoming contaminated fluid 124 meanders along the internal length of the reactor 120 by alternately flowing between channels 164 (formed by the numerous aligned fins 180) via the enlarged internal/central openings 155 of the baffle 150a and fins 180 (shown in FIGS. 11A and 11C, respectively) and then subsequently around the cut outside edges 152e/152f/152g/152h of the baffle 150b and cut outside edges 181e/181f/181g/181h of the fins 180 (shown in FIGS. 11B and 11C, respectively). These cut outside edges create gaps from the reactor's outside wall though which fluid is directed, and the expanded perimeter 158 of the enlarged central openings 155 allow the lamp of the mounting assembly 176 to be located therethrough, but leaves adequate space about the lamp to permit fluid flow therebetween. Alternating groupings of baffle/fins with enlarged central openings, and baffle/fins with cut outside edges, establish the desired meandering pathway 162. The fluid eventually exits this altered meandering pathway as a treated fluid stream 126 through the outlet port located at the opposed end of the reactor 120 from the incoming contaminated fluid 124, similarly to the earlier preferred embodiment.

The use of UVC light and highly reactive $TiO_2$ photocatalyst, in combination with the baffle and fin configuration of the present invention, provides increased fluid exposure time to UV light and coated surface areas, and effectively renders biological organisms inert, and to convert virtually all hazardous and noxious aromatic contaminants (chemical compounds considered detrimental to health, safety and the environment) into substantially lesser harmful elements of carbon dioxide ($CO_2$) gas and water ($H_2O$) vapour. $CO_2$ and $H_2O$ are already staple and essential elements in the atmosphere for the propagation of plant growth, and subsequently the generation of oxygen to sustain life. Thus, the comparatively small amount of $CO_2$ and $H_2O$ produced by the present invention can be considered environmentally beneficial rather than detrimental.

The present invention employs an 'Anatase $TiO_2$' photocatalytic coating on all baffle, fin and inside housing surfaces (including inlet and outlet connections, as required). In addition to having been designated physically and chemically safe and non-toxic, compared to other photocatalysts, it is also cost effective, convenient to apply, easily activated and readily available. Although a 'Rutile $TiO_2$' photocatalytic coating could be used, it is not preferred because UVC light penetration is limited to about 2 nm. This is less desirable when compared to the approximately 5 nm UVC light penetration allowance by 'Anatase $TiO_2$', for greater Hydroxyl Radical generation.

The reactor can accommodate different types of UV lights, such a UW and UVC-LED, for treating different types of contaminants as desired. The UW lamp could be used instead of the described combination of UVC lamp and $TiO_2$ coating, but has a number of drawbacks. Use of a UW lamp is generally not desired at this time as it is not as readily available as UVC lamps, is somewhat costlier than UVC lamps, generates Ozone (considered a health hazard) and has a shorter operating lifespan than a UVC lamp. UVC-LED lights have to date not been perfected for large area usage since they are still very costly, are very small in size and only about 5% of the supplied energy is converted to light, with the remaining 95% to heat.

Finally, it is noted that energizing the preferred UVC lamp produces short wavelengths, approx. $\lambda=254$ nm (nanometres) long, capable of instigating immediate photocatalytic oxidation by reacting with the $TiO_2$ photocatalytic coating applied to the surface areas of the baffles, fins and internal housing surfaces without generating any appreciable amount of Ozone. The minimal amount of Ozone produced, which would normally exist for hours and days, is destroyed inside the reactor by the Hydroxyl Radicals. The interaction of UVC light and TiO2 coating has been well documented. Furthermore, independent proof-of-concept test lab results have achieved toxic chemical destruction efficiencies, of such products as formaldehyde, benzene and ammonia (all associated with 'sick building syndrome), resulting in emission reductions in the 95% plus range.

The above description is intended in an illustrative rather than a restrictive sense, and variations to the specific configurations described may be apparent to skilled persons in adapting the present invention to other specific applications. Such variations are intended to form part of the present invention insofar as they are within the spirit and scope of the claims below.

We claim:

1. An apparatus for treatment of a contaminated fluid comprising:
    an elongate housing having a length and an inlet and an outlet in an outer wall or end thereof, wherein said inlet receives said contaminated fluid and creates at least one fluid stream thereof;
    at least one elongate energy source for emitting energy extending within said elongate housing along the length thereof;
    a plurality of baffles within said elongate housing arranged in a spaced relationship along the length of said elongate housing and extending radially between said at least one elongate energy source and said outer wall of said elongate housing, said plurality of baffles defining openings, wherein said openings alternate in location to create a meandering pathway for said at least one fluid stream from said inlet to said outlet to provide uninterrupted exposure to said energy from said at least one elongate energy source along a length of said meandering pathway;
    at least one fin located along a portion of said meandering pathway for subdividing said portion of said meandering pathway into a plurality of parallel flow channels, wherein an entirety of said at least one fin is arranged between two baffles or between a baffle and an end of said elongate housing; and
    a photocatalytic coating on said plurality of baffles, said at least one fin and inner surfaces of said outer wall of said elongate housing, wherein said inner surface of said outer wall of said elongate housing is within a pre-set radial distance of said at least one elongate energy source for exposure to said energy to activate a photocatalytic reactant, so that said contaminated fluid flowing through said meandering pathway, including said flow channels, is continuously maintained within said pre-set radial distance to said at least one elongate energy source and is provided adequate time flowing along said meandering pathway for combined exposure to said energy and said photocatalytic reactant to treat said contaminated fluid before exiting said elongate housing through said outlet.

2. The apparatus of claim 1 wherein said plurality of baffles and said at least one fin are planar thin plates.

3. The apparatus of claim 1 wherein said plurality of baffles and said at least one fin are removably positioned within said elongate housing.

4. The apparatus of claim 1 wherein holes within said plurality of baffles and said at least one fin are aligned for accepting said at least one elongate energy source therethrough when said plurality of baffles and said at least one fin are positioned within said elongate housing.

5. The apparatus of claim 1 wherein said parallel flow channels are arranged parallel to said portion of said meandering pathway to avoid obstructing flow of said fluid stream.

6. The apparatus of claim 2 wherein said parallel flow channels are arranged parallel to said portion of said meandering pathway to avoid obstructing flow of said fluid stream.

7. The apparatus of claim 1 wherein said photocatalytic coating comprises Titanium Dioxide.

8. The apparatus of claim 1 wherein said at least one elongate energy source comprises a lamp arrangement having an ultraviolet light source.

9. The apparatus of claim 4 wherein said at least one elongate energy source comprises a lamp arrangement having an ultraviolet light source.

10. The apparatus of claim 9 wherein said lamp arrangement includes a clear sleeve surrounding said ultraviolet light source to protect said ultraviolet light source by preventing contact with said contaminated fluid or to prevent injury if broken.

11. The apparatus of claim 8 wherein said pre-set radial distance is no greater than 75 mm to maintain activation of said photocatalytic reactant by ultraviolet light from said ultraviolet light source for effective treatment of said fluid.

12. The apparatus of claim 10 wherein said pre-set radial distance is no greater than 75 mm to maintain activation of said photocatalytic reactant by ultraviolet light from said ultraviolet light source for effective treatment of said fluid.

13. The apparatus of claim 9 wherein said pre-set radial distance is no greater than 75 mm to maintain activation of said photocatalytic reactant by ultraviolet light from said ultraviolet light source for effective treatment of said fluid.

14. The apparatus of claim 2 wherein said plurality of baffles and/or said at least one fin includes one or more perpendicular extensions to achieve consistent spacing between an adjacent baffle and/or fin.

15. The apparatus of claim 13 wherein said plurality of baffles and/or said at least one fin includes one or more perpendicular extensions to achieve consistent spacing between an adjacent baffle and/or fin.

16. An apparatus for treatment of a contaminated fluid comprising:

an elongate housing having a length and an inlet and an outlet in an outer wall or end of the elongate housing, wherein the inlet receives the contaminated fluid and creates at least one fluid stream;

at least one elongate energy source for emitting energy extending within the elongate housing along the length of the elongate housing;

a plurality of baffles arranged in a spaced relationship within the elongate housing and providing a series of baffle openings to create a meandering pathway for the at least one fluid stream from the inlet to the outlet to provide exposure to the energy from the at least one elongate energy source along the meandering pathway;

at least one fin located along a portion of the meandering pathway between two baffles of the plurality of baffles or between a baffle and an end of the elongate housing, the at least one fin subdividing the portion of the meandering pathway into a plurality of channels which subdivide the at least one fluid stream into multiple fluid streams, wherein at least one of the flow channels is between a first surface and a second surface which face one another, the first surface belonging to one of the baffles and the second surface belonging to the at least one fin; and a photocatalytic coating on the at least one fin comprising a photocatalytic reactant activated by the energy from the at least one elongate energy source, wherein the meandering pathway provides the contaminated fluid combined exposure to the energy and the photocatalytic reactant to treat the contaminated fluid before the meandering pathway reaches the outlet.

17. The apparatus of claim 16 wherein the at least one fin has an end at which the multiple fluid streams rejoin into a single fluid stream.

18. The apparatus of claim 16 wherein a total length of the meandering pathway is based on a total number of the plurality of baffles.

19. The apparatus of claim 16 wherein the at least one fin has a shared orientation with the plurality of baffles.

20. The apparatus of claim 16 wherein a direction of the meandering pathway on one side of a baffle of the plurality of baffles is opposite to a direction of the meandering pathway on an opposite side of the baffle.

* * * * *